(12) United States Patent
Huang et al.

(10) Patent No.: US 8,617,543 B2
(45) Date of Patent: Dec. 31, 2013

(54) MODIFIED MUTANT COLLAGENASE AND ITS USE IN FAT MELTING AND IN SCAR REDUCTION

(75) Inventors: Lan Huang, Bronx, NY (US); Yong Cang, San Diego, CA (US); Renato (Rene) Jose, Bridgewater, NJ (US)

(73) Assignee: Yolare Pharmaceuticals, LLC, Edison, NJ (US)

( * ) Notice: Subject to any disclaimer, the term of this patent is extended or adjusted under 35 U.S.C. 154(b) by 345 days.

(21) Appl. No.: 12/449,541

(22) PCT Filed: Feb. 13, 2008

(86) PCT No.: PCT/CN2008/000333
§ 371 (c)(1),
(2), (4) Date: Aug. 12, 2009

(87) PCT Pub. No.: WO2008/101406
PCT Pub. Date: Aug. 28, 2008

(65) Prior Publication Data
US 2012/0164131 A1    Jun. 28, 2012

Related U.S. Application Data

(60) Provisional application No. 60/901,145, filed on Feb. 14, 2007.

(51) Int. Cl.
*A61K 38/46* (2006.01)
*C12N 9/00* (2006.01)

(52) U.S. Cl.
USPC ........................................ 424/94.67; 435/183

(58) Field of Classification Search
None
See application file for complete search history.

(56) References Cited

PUBLICATIONS

Jung et al., "Identification of Metal Ligands in the Clostridium histolyticum ColH Collagenase", Journal of Bacteriology, 1999, vol. 181, No. 9, pp. 2816-2822.*

* cited by examiner

*Primary Examiner* — Suzanne M Noakes
(74) *Attorney, Agent, or Firm* — Hamre, Schumann, Mueller & Larson, P.C.

(57) ABSTRACT

A *Clostridium histolyticum* collagenase ColH (Glu451Asp) melts adipose tissue when injected into selected regions of the body. This protein product melts fat pads effectively in fat rat experiments, with very little side effects. Very little hemorrhage was observed. We also invent a new version of ColH mutant by linking a peptide motif CKGGRAKDC-G (varying from 2 to 6 Gs) (SEQ ID NO: 2) in front of ColH (Glu451Asp) (called topical ColH-FM), which can target to white fat vasculature. By combining with novel transdermal technology (such as Hydroxysome technology), we develop a topical protein cream that can melt fat. This product can be used as cellulite cream and for chemical liposuction. This topical ColH-FM can also be injected into adipose tissue as a replacement for liposuction or as an adjunct method with liposuction. Since raise scar is formed by overgrowth of collagen, our topical ColH-FM cream is shown to have application in scar reduction.

16 Claims, 8 Drawing Sheets

A) Protein Sequence

1. Mutant ColH (E451D) after cutting

* GS from GST-ColH(E451D) cutting
GSVQNESKRYTVSYLKTLNYYDLVDLLVKTEIENLPDLFQYSSDAKEFYGNKTRMS
FIMDEIGRRAPQYTEIDHKGIPTLVEVVRAGFYLGFHNKELNEINKRSFKERVIPSILA
IQKNPNFKLGTEVQDKIVSATGLLAGNETAPPEVVNNFTPILQDCIKNIDRYALDDL
KSKALFNVLAAPTYDITEYLRATKEKPENTPWYGKIDGFINELKKLALYGKINDNN
SWIIDNGIYHIAPLGKLHSNNKIGIETLTEVMKVYPYLSMQHLQSADQIKRHYDSKD
AEGNKIPLDKFKKEGKEKYCPKTYTFDDGKVIIKAGARVEEEKVKRLYWASKEVNS
QFFRVYGIDKPLEEGNPDDILTMVIYNSPEEYKLNSVLYGYDTNNGGMYIEPEGTFF
TYEREAQESTYTLEELFRHEYTHYLQGRYAVPGQWGRTKLYDNDRLTWYEEGGAD
LFAGSTRTSGILPRKSIVSNIHNTTRNNRYKLSDTVHSKYGASFEFYNYACMFMDY
MYNKDMGILNKLNDLAKNNDVDGYDNYIRDLSSNYALNDKYQDHMQERIDNYE
NLTVPFVADDYLVRHAYKNPNEIYSEISEVAKLKDAKSEVKKSQYFSTFTLRGSYTG
GASKGKLEDQKAMNKFIDDSLKKLDTYSWSGYKTLTAYFTNYKVDSSNRVTYDV
VFHGYLPNEGDSKNSLPYGKINGTYKGTESSVSTTTAEIKDLSENKLPVIYMHVPKS
GALNQKVVFYGKGTYDPDGSIAGYQWDFGDGSDFSSEQNPSHVYTKKGEYTVTL
RVMDSSGQMSEKTMKIKITDPVYPIGTEKEPNNSKETASGPIVPGIPVSGTIENTSDQ
DYFYFDVITPGEVKIDINKLGYGGATWVVYDENNNAVSYATDDGQNLSGKFKADK
PGRYYIHLYMFNGSYMPYRINIEGSVGR

Fig. 1A

2. Modified ColH (E451D)(ColH-FM)

* GS from GST-ColH(E451D) cutting, CKGGRAKDC as signal peptide homing onto the white fat cell, GG as the linker.
GS-CKGGRAKDC-GG-VQNESKRYTVSYLKTLNYYDLVDLLVKTEIENLPDLFQYS SDAKEFYGNKTRMSFIMDEIGRRAPQYTEIDHKGIPTLVEVVRAGFYLGFHNKELN EINKRSFKERVIPSILAIQKNPNFKLGTEVQDKIVSATGLLAGNETAPPEVVNNFTPIL

QDCIKNIDRYALDDLKSKALFNVLAAPTYDITEYLRATKEKPENTPWYGKIDGFINE
LKKLALYGKINDNNSWIIDNGIYHIAPLGKLHSNNKIGIETLTEVMKVYPYLSMQHL
QSADQIKRHYDSKDAEGNKIPLDKFKKEGKEKYCPKTYTFDDGKVIIKAGARVEEE
KVKRLYWASKEVNSQFFRVYGIDKPLEEGNPDDILTMVIYNSPEEYKLNSVLYGYD
TNNGGMYIEPEGTFFTYEREAQESTYTLEELFRHEYTHYLQGRYAVPGQWGRTKLY
DNDRLTWYEEGGADLFAGSTRTSGILPRKSIVSNIHNTTRNNRYKLSDTVHSKYGA
SFEFYNYACMFMDYMYNKDMGILNKLNDLAKNNDVDGYDNYIRDLSSNYALND
KYQDHMQERIDNYENLTVPFVADDYLVRHAYKNPNEIYSEISEVAKLKDAKSEVKK
SQYFSTFTLRGSYTGGASKGKLEDQKAMNKFIDDSLKKLDTYSWSGYKTLTAYFT
NYKVDSSNRVTYDVVFHGYLPNEGDSKNSLPYGKINGTYKGTESSVSTTTAEIKDL
SENKLPVIYMHVPKSGALNQKVVFYGKGTYDPDGSIAGYQWDFGDGSDFSSEQNP
SHVYTKKGEYTVTLRVMDSSGQMSEKTMKIKITDPVYPIGTEKEPNNSKETASGPIV
PGIPVSGTIENTSDQDYFYFDVITPGEVKIDINKLGYGGATWVVYDENNNAVSYATD
DGQNLSGKFKADKPGRYYIHLYMFNGSYMPYRINIEGSVGR

Fig. 1B

B) DNA sequence

1. Open Reading Frame of Mutant ColH (E451D)

```
 421 gtacaaaatg aaagtaagag gtatacagta tcatatttaa agactttaaa ttattatgac
 481 ttagtagatt tgcttgttaa gactgaaatt gagaatttac cagaccttt tcagtatagt
 541 tcagatgcaa aagagttcta tggaaataaa actcgtatga gctttatcat ggatgaaatt
 601 ggtagaaggg cacctcagta tacagagata gatcataaag gtattcctac tttagtagaa
 661 gttgtaagag ctggatttta cttaggattc cataacaagg aattgaatga aataaacaag
 721 aggtcttta aagaaagggt aataccttct atattagcaa ttcaaaaaaa tcctaatttt
 781 aaactaggta ctgaagttca agataaaata gtatctgcaa caggactttt agctggtaat
 841 gaaacagcgc ctccagaagt tgtaaataat tttacaccaa tacttcaaga ctgtataaag
 901 aatatagaca gatacgctct tgatgattta aagtcaaaag cattatttaa tgttttagct
 961 gcacctacct atgatataac tgagtattta agagctacta aagaaaaacc agaaaacact
1021 ccttggtatg gtaaaataga tgggttata aatgaactta aaaagttagc tctttatgga
1081 aaaataaatg ataataactc ttggataata gataacggta tatatcatat agcacccttta
1141 gggaagttac atagcaataa taaaatagga atagaaactt taacagaggt tatgaaagtt
1201 tatccttatt taagtatgca acatttacaa tcagcagatc aaattaagcg tcattatgat
1261 tcaaaagatg ctgaaggaaa caaaatacct ttagataagt ttaaaaagga aggaaaagaa
```

Fig. 1C

```
1321 aaatactgtc caaaaactta tacatttgat gatggaaaag taataataaa agctggtgct
1381 agagtagaag aagaaaaagt taaaagacta tactgggcat caaaggaagt taactctcaa
1441 ttctttagag tatacggaat agacaaacca ttagaagaag gtaatccaga tgatatatta
1501 acaatggtta tctacaacag tcccgaagaa tataaactca atagtgttct atacggatat
1561 gatactaata atggtggtat gtatatagag ccagaaggaa ctttcttcac ctatgaaaga
1621 gaagctcaag aaagcacata cacattagaa gaattattta gacatgaata tacacattat
1681 ttgcaaggaa gatatgcagt tccaggacaa tggggaagaa caaaacttta tgacaatgat
1741 agattaactt ggtatgaaga aggtggagca gaTttatttg caggttctac tagaacttct
1801 ggaatattac caagaaagag tatagtatca aatattcata atacaacaag aaataataga
1861 tataagcttt cagacactgt acattctaaa tatggtgcta gttttgaatt ctataattat
1921 gcatgtatgt ttatggatta tatgtataat aaagatatgg gtatattaaa taaactaaat
1981 gatcttgcaa aaaataatga tgttgatgga tatgataatt atattagaga tttaagttct
2041 aattatgctt taaatgataa atatcaagat catatgcagg agcgcataga taattatgaa
2101 aatttaacag tgccttttgt agctgatgat tatttagtaa ggcatgctta taagaaccct
2161 aatgaaattt attctgaaat atctgaagta gcaaaattaa aggatgctaa gagtgaagtt
2221 aagaaatcac aatatttag tacctttact ttgagaggta gttacacagg tggagcatct
2281 aaggggaaat tagaagatca aaaagcaatg aataagttta tagatgattc acttaagaaa
2341 ttagatacgt attcttggag tgggtataaa actttaactg cttatttcac taattataaa
2401 gttgactctt caaatagagt tacttatgat gtagtattcc acggatattt accaaacgaa
2461 ggtgattcca aaaattcatt accttatggc aagatcaatg gaacttacaa gggaacagag
2521 aaagaaaaaa tcaaattctc tagtgaaggc tctttcgatc cagatggtaa aatagtttct
```

Fig. 1D 2581 tatgaatggg atttcggaga tggtaataag agtaatgagg aaaatccaga gcattcatat
2641 gacaaggtag gaacttatac agtgaaatta aaagttactg atgacaaggg agaatcttca
2701 gtatctacta ctactgcaga aataaaggat ctttcagaaa ataaacttcc agttatatat
2761 atgcatgtac ctaaatccgg agccttaaat caaaaagttg ttttctatgg aaaaggaaca
2821 tatgacccag atggatctat cgcaggatat caatgggact ttggtgatgg aagtgatttt
2881 agcagtgaac aaaacccaag ccatgtatat actaaaaaag gtgaatatac tgtaacatta
2941 agagtaatgg atagtagtgg acaaatgagt gaaaaaacta tgaagattaa gattacagat
3001 ccggtatatc caataggcac tgaaaaagaa ccaaataaca gtaaagaaac tgcaagtggt
3061 ccaatagtac caggtatacc tgttagtgga accatagaaa atacaagtga tcaagattat
3121 ttctattttg atgttataac accaggagaa gtaaaaatag atataaataa attagggtac
3181 ggaggagcta cttgggtagt atatgatgaa aataataatg cagtatctta tgccactgat
3241 gatgggcaaa atttaagtgg aaagttttaag gcagataaac caggtagata ttacatccat 3301 ctttacatgt ttaatggtag ttatatgcca tatagaatta atatagaagg ttcagtagga
3361 agataa

Fig. 1E

2. Open Reading Frame of Modified ColH (E451D) (ColH-FM)

```
     tgtaagggaggaagagctaaggattgtggagga
421  gtacaaaatg aaagtaagag gtatacagta tcatatttaa agactttaaa ttattatgac
481  ttagtagatt tgcttgttaa gactgaaatt gagaatttac cagacctttt tcagtatagt
541  tcagatgcaa aagagttcta tggaaataaa actcgtatga gctttatcat ggatgaaatt
601  ggtagaaggg caccctcagta tacagagata gatcataaag gtattcctac tttagtagaa
661  gttgtaagag ctggattta cttaggattc cataacaagg aattgaatga aataaacaag
721  aggtcttta aagaaagggt aataccttct atattagcaa ttcaaaaaaa tcctaatttt
781  aaactaggta ctgaagttca agataaaata gtatctgcaa caggactttt agctggtaat
841  gaaacagcgc ctccagaagt tgtaaataat tttacaccaa tacttcaaga ctgtataaag
901  aatatagaca gatacgctct tgatgattta aagtcaaaag cattatttaa tgtttagct
961  gcacctacct atgatataac tgagtattta agagctacta aagaaaaacc agaaaacact
1021 ccttggtatg gtaaaataga tgggtttata aatgaactta aaaagttagc tctttatgga
1081 aaaataaatg ataataactc ttggataata gataacggta tatatcatat agcaccttta
1141 gggaagttac atagcaataa taaaatagga atagaaactt taacagaggt tatgaaagtt
1201 tatccttatt taagtatgca acatttacaa tcagcagatc aaattaagcg tcattatgat
1261 tcaaaagatg ctgaaggaaa caaaatacct ttagataagt ttaaaaagga aggaaaagaa
1321 aaatactgtc caaaaactta tacatttgat gatggaaaag taataataaaa agctggtgct
1381 agagtagaag aagaaaaagt taaaagacta tactgggcat caaaggaagt taactctcaa
1441 ttctttagag tatacggaat agacaaaacca ttagaagaag gtaatccaga tgatatatta
1501 acaatggtta tctacaacag tcccgaagaa tataaactca atagtgttct atacggatat
1561 gatactaata atggtggtat gtatatagag ccagaaggaa ctttcttcac ctatgaaaga
```

Fig. 1F 1621 gaagctcaag aaagcacata cacattagaa gaattattta gacatgaata tacacattat
1681 ttgcaaggaa gatatgcagt tccaggacaa tggggaagaa caaaacttta tgacaatgat
1741 agattaactt ggtatgaaga aggtggagca gaTttatttg caggttctac tagaacttct
1801 ggaatattac caagaaagag tatagtatca aatattcata atacaacaag aaataataga
1861 tataagcttt cagacactgt acattctaaa tatggtgcta gttttgaatt ctataattat
1921 gcatgtatgt ttatggatta tatgtataat aaagatatgg gtatattaaa taaactaaat
1981 gatcttgcaa aaaataatga tgttgatgga tatgataatt atattagaga tttaagttct 2041 aattatgctt taaatgataa atatcaagat catatgcagg agcgcataga taattatgaa
2101 aatttaacag tgccttttgt agctgatgat tatttagtaa ggcatgctta taagaaccct
2161 aatgaaattt attctgaaat atctgaagta gcaaaattaa aggatgctaa gagtgaagtt
2221 aagaaatcac aatatttag tacctttact ttgagaggta gttacacagg tggagcatct
2281 aaggggaaat tagaagatca aaaagcaatg aataagttta tagatgattc acttaagaaa
2341 ttagatacgt attcttggag tgggtataaa actttaactg cttatttcac taattataaa
2401 gttgactctt caaatagagt tacttatgat gtagtattcc acggatattt accaaacgaa
2461 ggtgattcca aaaattcatt accttatggc aagatcaatg gaacttacaa gggaacagag
2521 aaagaaaaaa tcaaattctc tagtgaaggc tctttcgatc cagatggtaa aatagtttct
2581 tatgaatggg atttcggaga tggtaataag agtaatgagg aaaatccaga gcattcatat
2641 gacaaggtag gaacttatac agtgaaatta aaagttactg atgacaaggg agaatcttca
2701 gtatctacta ctactgcaga aataaaggat ctttcagaaa ataaacttcc agttatatat
2761 atgcatgtac ctaaatccgg agccttaaat caaaaagttg ttttctatgg aaaaggaaca
2821 tatgacccag atggatctat cgcaggatat caatgggact tggtgatgg aagtgatttt

Fig. 1G 2881 agcagtgaac aaaacccaag ccatgtatat actaaaaaag gtgaatatac tgtaacatta 2941 agagtaatgg atagtagtgg acaaatgagt gaaaaaacta tgaagattaa gattacagat 3001 ccggtatatc caataggcac tgaaaaagaa ccaaataaca gtaaagaaac tgcaagtggt 3061 ccaatagtac caggtatacc tgttagtgga accatagaaa atacaagtga tcaagattat 3121 ttctattttg atgttataac accaggagaa gtaaaaatag atataaataa attagggtac 3181 ggaggagcta cttgggtagt atatgatgaa aataataatg cagtatctta tgccactgat 3241 gatgggcaaa atttaagtgg aaagtttaag gcagataaac caggtagata ttacatccat 3301 ctttacatgt ttaatggtag ttatatgcca tatagaatta atatagaagg ttcagtagga 3361 agataa

Fig. 1H

MODIFIED MUTANT COLLAGENASE AND ITS USE IN FAT MELTING AND IN SCAR REDUCTION

PRIORITY CLAIM

This application is a §371 application of PCT/CN2008/000333 that was filed on Feb. 13, 2008, which claims priority from the U.S. Provisional Application Nos. 60/901,145, filed on Feb. 14, 2007, now expired.

FIELD OF THE INVENTION

The invention relates to Modified mutant collagenase for fat melting application and for scar reduction application.

SEQUENCE LISTING

The instant application contains a Sequence Listing which has been submitted in ASCII format via EFS-Web and is hereby incorporated by reference in its entirety. Said ASCII copy, created on Jan. 30, 2012, is named 8254002.txt and is 26,614 bytes in size.

BACKGROUND OF THE INVENTION

1) Fat Reduction

Obesity is becoming a huge problem for appearance and for health. Many pharmaceutical companies are developing drugs for people to lose weight. Liposuction is one major remedy to get rid of excess fat, with 700,000 operations each year in the US. However, liposuction is very invasive and cause major side effects. Cellulite cream is a non-invasive method to improve appearance of body areas, which have excess fat. But there is no effective cellulite cream out on the market. The current cellulite cream potentially shrinks the fat cells temporarily, not eliminating them.

Liposuction is a procedure that removes fat under skin mechanically using vacuum (at one negative atmosphere). Cosmetic industry uses liposuction to remove excess fat at specific areas of the male and female human body. Liposuction easily causes infection, bruises, contour deformity, and mechanical damage to tissue under skin. Thus liposuction using mechanical force is not desirable.

Cellulite is a big problem for people. While the current crop of products claiming to reduce or eliminate cellulite is rapidly increasing, research regarding their efficacy remains at a bare minimum. Overall, the research states loud and clear these products don't work but sadly, the lure of these potions is hard to fend off. In fact, according to the American Academy of Dermatology, cellulite is the body's natural way of storing fat in adult women. For some women, especially very thin women, cellulite may only be visible by pinching skin, while for the vast majority of women, some amount of cellulite is always visible.

Cellulite is assumed to be caused by the accumulation of fat cells that protrude or are interlaced with possibly weakened layers of skin. Many companies selling anti-cellulite products have referred to this as "imprisoned fat," which is actually a decent analogy. What is definitely true is that women are far more prone to cellulite than men, most likely because they have more subcutaneous fat cells in their hips and thighs (Source: Journal of Applied Physiology, April 2002, pages 1611-1618).

There is a lengthy list of products claiming they can be rubbed on the skin and then some how free body fat and improve skin tone to eliminate or reduce the appearance of cellulite. Despite the popularity of these lotions and potions, two questions remain unresolved: (1) the lack of any formulary cohesiveness between products, and (2) any support that these products work (Source: Skin Research and Technology, May 2002, pages 118-124). The European Journal of Dermatology (December 2000, pages 596-603) reviewed 32 cellulite products containing between 4 and 31 ingredients that had few similarities. "Forty-four different botanicals and 39 different emollients were used in the 32 products. Caffeine, present in 14 products, was the most common additive, apparently representing an 'active' ingredient. In other respects the compositions of the products were similar to those of skin creams." Cosmetics companies are throwing in random plants without any proof they can help, and yet the suggestive claims are there to entice consumers to try yet another miracle anti-cellulite potion.

Aminophylline, a prescription bronchodilator (opens lung passageways), gained notoriety as an ingredient in cellulite creams as a result of a study published in Obesity Research (November 1995, Supplemental pages 561S-568S). However, doubt about aminophylline's value was revealed by a study published in Plastic and Reconstructive Surgery (September 1999, pages 1110-1114), which described a double-blind study that compared the effectiveness of three different treatments for cellulite on three different groups of women. So, aminophylline appears not to be the answer for cellulite, though it still shows up in some cellulite creams.

Caffeine is used as an ingredient in cellulite creams because of its distant relationship to aminophylline. There are two studies showing caffeine to have benefit for cellulite, but one was conducted by Johnson & Johnson, which owns RoC and Neutrogena, both companies that sell cellulite creams that contain caffeine, and the other was conducted by cosmetic ingredient manufacturers that sell anti-cellulite compounds (Source: Journal of Cosmetic Science, July-August 2002, pages 209-218). There is no other independent research showing that caffeine provides any benefit for treating cellulite, nor research pointing to how much caffeine is needed to produce results.

2) Scar Reduction

Scar is formed by overgrowth of collagen after wound healing. Most of the scar reduction products contain silicone in a sheet or gel format, and onion extracts (Mederma Skin Care products). It usually takes over 3 months to see some effect, because these products do not contain effective active ingredient such as any form of collagenase which targets the cause of scar formation.

BRIEF SUMMARY OF THE INVENTION

The invention relates to a composition comprising a modified single mutant collagenase ColH-FM, wherein the ColH-FM is a *Clostridium histolyticum* collagenase ColH (Glu451Asp), with additional peptide motif CKGGRAKDC-G(n), SEQ ID NO: 2, in front of ColH (Glu451Asp), n is 2 to 6. The composition can further comprise carrier that is pharmaceutically acceptable, such as those selected from the group consisting of normal saline, aqueous dextran solution, and aqueous hetastarch solution.

In another aspect, the invention provides a use of ColH-FM in making medicine for reducing the amount of adipose tissue at selected locations in the body, which comprises introducing into said medicine effective amounts of single ColH-FM or the same mutant collagenase plus a N-terminal tag of CKGGRAKDC-G, SEQ ID NO: 2, varying from 2 to 6 Gs or any other peptide which can target to white fat vasculature in human and in animals. Furthermore, the ColH-FM can be used in making medicine for reduction and removal of lipomas, and making medicine for scar reduction.

The invention also relates to a method of reducing the amount of adipose tissue at selected locations in the body, which comprises introducing into said tissue effective amounts of a mutant collagenase or the same mutant collagenase plus a N-terminal tag of CKGGRAKDC-G, SEQ ID NO: 2, (varying from 2 to 6 Gs) or any other peptide which can target to white fat vasculature in human and in animals. In an embodiment, said adipose tissue is subcutaneous. Preferably, the mutant full length ColH is from *Clostridium histolyticum*. In an embodiment, said mutant ColH is at E451D. In detail, Glutamate at position 451 of ColH is mutated to Aspartate in the stretch of sequence (440DRLTWYEEG-GAE451, SEQ ID NO: 3), wherein the activity of ColH mutant is 20% of wild type ColH. Or said mutant ColH is at Glu451 changed to any other residue in 20 amino acids selections, specifically E451A and E451Q. In an embodiment, said mutant collagenase in a pharmaceutically acceptable carrier is injected into said adipose tissue, preferably a solution of mutant Collagenase in a liquid pharmaceutically acceptable carrier is injected, and preferably said carrier is aqueous, more preferably said adipose tissue is subcutaneous and said solution is injected percutaneously at one site or a multiplicity of closely spaced sites. In another embodiment, said modified mutant collagenase in a topical pharmaceutical acceptable carrier which can be delivered into white fat cells under skin or raised scar by transdermal technology, such as Hydroxysome technology. In still another embodiment, the mutant collagenase is introduced in the amount from about 1 to 30 ABC units mutant collagenase (1-50 unit per fat pad in fat rat) per gram of adipose tissue treated. Collagenase ABC activity unit is calculated using Worthington Biochem's collagnease assay protocol (5 hours of incubation) at 37 C. Preferably the mutant collagenase is introduced in a liquid pharmaceutically acceptable carrier in a concentration of from 5 to about 500 ABC units per ml. Also preferably the mutant collagenase is introduced in a topical cream pharmaceutically acceptable carrier in a concentration of from 5 to about 500 ABC units per ml. In another embodiment, said mutant collagenase in a pharmaceutically acceptable carrier is injected into said lipoma. Said mutant collagenase in a pharmaceutically acceptable carrier is injected into fat pad as a chemical liposuction agent.

According to the invention, the mutant collagenase of the invention in the company of transdermal technology can be used as a cellulite cream, or topical cream which replaces liposuction, or can be used as a scar reduction cream.

In other words, the invention provides a new method to obtain the reduction of excess amounts of unaesthetic and/or redundant subcutaneous adipose tissue with non-invasive method, such as injection or topical cream. The product can be used as chemical liposuction agent by injection or topical cellulite cream. When bio-engineered mutant ColH is introduced into subcutaneous adipose tissue of a living animal body, a dissociation and reduction of the adipose tissue at that location occurs. This method is gentle and precise, which does not induce trauma to human body, and does not cause infection.

This invention is also intended to the reduction and removal of lipomas, whether found at the surface of the skin, within the skin, subcutaneous, or anywhere else in the body. Lipomas are generally benign tumors of fatty tissues. Currently, lipomas are removed with surgery, which potentially cause pain and hematoma to patients undergoing the operation. The present invention avoids these problems by introducing into lipoma(s) effective amounts of mutant ColH. This mutant protein is more stable than wild type ColH, yet has lower activity. It melts fat in a slow and mellow fashion, and little bleeding is observed in fat rat dissection experiments. ColH mutant can be developed into a pharmaceutical because it is a single identity, and it is easy for the CMC (chemical manufacture control).

Additional application for this invention is scar reduction, whether found at the surface of the skin. Mutant collagenase can digest over-grown collagen in the raised scar tissue, and thus decrease the height and appearance of scar.

Collagenase purified from regular commercial sources (also from *Clostridium histolyticum*) is a mixture of 5-6 collagenases. Even if it is highly purified, ColH and ColG, with similar molecular weight and iso-electric points (PIs), are very hard to separate. Thus the highly purified version of collagnease from *Clostridium histolyticum* still contains a mixture of ColG and ColH. Wild type collagenase purified from regular process induces large amount of bleeding in our fat rat experiments.

The invention may also be used for the treatment of lipomas and other adipose tissues in humans and in animals, in wild life, in human homes, or in zoos.

DETAILED DESCRIPTION

Human has a layer of adipose tissue, composed largely of linked fat cells under our skin. Our invention can reduce the amount of adipose tissue under our skin by introducing into the tissue effective amounts of single mutant ColH (*Clostridium histolyticum*). In the patent from Advance Tissues, they use a mixture of collagenase from *Clostridium histolyticum*, which induces large bleeding in our rat experiments.

1) Mutant ColH's Basis for Lower Activity in Digesting Collagen

The *Clostridium histolyticum* collagenase has been widely used for the disintegration of connectible tissue and separation of tissue culture cells, because of its broad substrate specificity and its abundance in culture filtrates (Seglen, P. O. 1976. Preparation of isolated rat liver cells. Methods Cell Biol. 13: 29-83). However, at least six different forms with molecular masses ranging from 68 to 125 kD are present in a commercial preparation (Bond, M. D., and Van Wart, H. E., 1984, Characterization of individual collagenases from *Clostridium histolyticum*. Biochemistry 23: 3085-3091). The difficulty in separating individual enzymes and the lot-to-lot variation of commercial collagenase preparations limit its practical use. Chemical Manufacturing Control (CMC) is quite important in drug development. Each batch of preparation has to be consistent. Thus this difficulty of purification brings potential problems in using collagnease directly purified from *Clostridium histolyticum* as pharmaceuticals for human use.

ColH gene encode 116 kD collagenase (Yoshihara, K., Matsushita, O., Minami, J., and Okabe, A. Cloning and nucleotide sequence analysis of the colH gene from *Clostridium histolyticum* encoding a collagnease and a gelatinase. J. Bacteriol. 176: 6489-6496). At its C-terminus, ColH has a 110-residue collagen-binding domain (Wilson, J. J., Matsushita, O., Okabe, A., and Sakon, J. A bacterial collagen-binding domain with novel calcium-binding motif controls domain orientation, EMBO, J. 2003, 22 (8): 1743-1752), which binds to insoluble type I collagen in vitro (Matsushita, O., Yoshihara, K., Katayama, S.-I., Minami, J., and Okabe, A. 1994. Purification and characterization of a *Clostridium histolyticum* 120-kilodalton collagenase and nucleotide sequence of the corresponding gene. J. Bacteriol. 176: 149-156) and also to collagen fibers in vivo (Nishi, N., Matsushita, K., Yuube, H., Miyanaka, A., Okabe, A., and Wada, F. 1998. Collagen-binding growth factors: production and characterization of functional fusion proteins having a collagen-binding domain. Proc. Natl. Acad., Sci. USA 95: 7018-7023). Thus ColH is quite specific in cutting collagen between fat cells. ColH is able to cleave peptide bonds on the amino side of the glycine residue in PXGP sequence (Peterkofsky, B., 1982. Bacterial collagenase. Methods Enzymol. 82: 453-471). Studies by atomic absorption spectrophotometry and metal replacement with chelators have show that ColH contains one catalytically essential zinc atom per molecule (Angelton, E. L., and Van Wart, H. E. 1988. Preparation and reconstitution with divalent metal ions of class I and class II *Clostridium histolyticum* appocollagenases. Biochemistry 27: 7406-7412), thus ColH is considered a zinc metalloproteinase.

The N-terminal 80 kD contains the active site of ColH (Matsushita, O., Jung, C.-M., Minami, J., Katayama, S., Nishi, N., and Okabe A. 1998. A study of the collagenase-binding domain of a 116-kDa *Clostridium histolyticum* collagenase. J. Biol. Chem. 273: 3643-3648). This peptide contains the sequence HEXXH, SEQ ID NO: 14, the zincin consensus motif, which is present in most zinc metalloproteinase (zincin). The zincin superfamily includes the vertebrate collagenases (matrix metalloproteinases [MMPs] as the matrixin subfamily. The alignment of amino acid sequences of isoforms of collagenase ColA, ColG and ColH reveals that they conserve the sequence $E^{446}$(D at ColG)$E^{447}XXXE^{451}$, SEQ ID NO: 16, C-terminal to the zincin motif. This could be another binding site for Zinc. Thus when we were looking for a ColH with lower activity than the wild type one, we targeted at HEXXXH, SEQ ID NO: 15, and $E^{446}EXXXE^{451}$, SEQ ID NO: 16.

According to Jung et al. (Jung, C.-M. et al. Identification of metal ligands in the *Clostridium histolyticum* ColH collagnease, J. Bacteriology, 1999 May: 2816-2822), the Km values of ColH with E446A and E451A mutations, which decreases enzymatic activity the most of all the Glu446 and Glu451 mutants, were not changed significantly (P, 0.957 and 0.91, respectively), indicating that their substrate (e.g. collagen) binding is not impaired. Therefore, it seems that the mutations do not alter the global three-dimensional structure of the enzyme. On the other hand, their Kcat values decreases significantly, indicating that the catalysis was impaired. Thus our selected mutant ColH E451D binds to its substrate collagen in a normal fashion. It has lower catalytic activity, which means that it cuts collagen slower than wild type ColH. (Note: Km is defined as true dissociation constant of the enzyme substrate complex; Kcat is defined as first order rate constant for the chemical conversion of the Enzyme-substrate complex to the enzyme-product complex). The proposed structure of the catalytic center of ColH is shown in FIG. 2.

2) Injection of Mutant ColH into the Fat Cells

It is within the skill of the art to select carriers that are pharmaceutically acceptable, including inertness towards the mutant ColH. Examples are normal saline, aqueous dextran solution, and aqueous hetastarch solution, preferably suitably buffered to neutral pH. One can use as carrier fibrin glue, comprising fibrin or fibrin precursors, e.g. fibrinogen plus thrombin; see U.S. Pat. No. 5,279,825. Again, selection of carrier and methods of preparing formulations are within the skill of the art. Though water and Calcium ions are necessary to activate the enzymes, the aqueous interstitial fluid present in the subcutaneous tissues is sufficient to do this. The above carriers are suitable for injection delivery of mutant ColH in claim 1.

The physician will first select what location(s) in the body she/he wishes to treat. In order to limit the amount of enzymes introduced into the body at one time and to permit a preliminary evaluation of results, a limited area—which may be less than the total area—may be chosen for initial treatment. The treatment solution is injected percutaneously into the subcutaneous adipose tissues, preceded if the physician or patient so desires with a light local anesthesia. For maximum effect from a given quantity of the enzyme solution it should be injected in small quantities at a multiplicity of closely spaced points in the area, preferably spaced not more than about two centimeters apart and even much closer. The best effects are achieved with injections spaced out with time, such as one injection every 3 days or one injection every week for 2 or 3 times.

Our mutant ColH is derived from bio-engineered Coal strain, using *E. Coli* as host. The potency assay of mutant ColH is based on the digestion of undenatured collagen (from bovine tendon) at pH 7.2 and 37.degree. C. for 5 hours. The number of peptide bonds cleaved is measured by reaction with ninhydrin. Amino groups released by a trypsin digestion control are subtracted. One net ABC unit of collagenase will solublize ninhydrin reactive material equivalent to 1.09 nanomoles of leucine per minute.

Concentrations of enzymes in the pharmaceutically acceptable carrier are chosen on the principle that sufficient liquid is present to diffuse adequately in the subcutaneous fatty tissue yet no more than adequate to carry the desired amount of actives into the area under treatment. A range from about 50 to 500 ABC units collagenase per ml is suitable and considerable latitude within and beyond this range is possible in making the choice for a given situation. Since diffusion into the adipose tissue and the freeing of fat therefrom is seldom complete, it is often desirable to repeat the treatment at least once. This can be done after a few days, for example 3 days or one week.

Injection of mutant collagenase in claim 1 can replace liposuction or be used as an adjunct to liposuction. The treatment is directed to sufficient disruption of the adipose tissue to make it easier to remove by suction. The liposuction stage will follow the application of the invention by one to three days.

Lipomas are normally removed by surgery or liposuction. By use of mutant ColH, the lipomatous tumor can be completely removed. The procedures, carriers, dosages and concentrations described above are applicable to the treatment of lipomas.

3) Topical Anti-Cellulite and Scar Reduction Cream

The modified mutant ColH in claim 1 can be delivered into the fat cells topically with the right transdermal delivery method. The signal peptide that homes the mutant collagenase to the fat cell vasculature helps to by-pass all the collagen in the skin (Nature Medicine 10(6), p625-632, 2004). 70% of human protein is made of collagen. Thus this signal peptide would eliminate side effect of a topical collagenase variant in disturbing the skin structure.

So far very few transdermal technology exists for delivering large proteins into the skin, especially if it is larger than 40 kD. Our modified mutant collagenase is as large as 120 kD. However, one novel transdermal technology using Hydroxysome, or ceramic hydroxyapatite (chemically pure calcium phosphate, U.S. Pat. No. 6,096,324 and U.S. Pat. No. 6,120,782) is able to deliver large proteins, such as 900 KD collagen into epidermis, dermis and fat cell region. Thus in combination with the right transdermal delivery method, our modified mutant collagenase is an effective anti-cellulite cream, which gets to the fat cells and melts fat effectively.

In addition, in combination with the right transdermal delivery method, our modified mutant collagenase is an effective scar reduction cream, which slowly digests over-grown collagen in the scar tissue.

DESCRIPTION OF FIGURES

FIG*s*. 1A to 1H describe Mutant ColH (E451D) and modified mutant ColH (E451D) (ColH-FM) protein and DNA sequences. In particular, FIG. 1A shows SEQ ID NO: 10, FIG. 1B shows SEQ ID NOS: 10 and 11, FIGS. 1C-1E show SEQ ID NO: 12, and FIGS. 1F-1H show SEQ ID NO: 13.

FIG. 2 describes proposed active site of ColH. The zinc-coordinating bonds and hydrogen bonds are indicated by thick arrows and dotted lines, respectively. Thin arrows represent the first steps of the mechanism of action (Derived from J. Bacteriology, May 1999, p. 2816-2822).

FIG. 3 is the electrophoresis photo with 7.5% PAGE gel of purified ColH (E451D) and stability results of wild type ColH and mutant ColH (E451D). Native ColH (10 ug) was incubated with Trypsin (1 ug) at lane 1, incubated with Trypsin (2 ug) at lane 2 both for 1 hour at 4 C. ColH (E451D, 10 ug) was incubated with Trypsin (0.5 ug) at lane 3, incubated with Trypsin (1 ug) at lane 4, incubated with Trypsin (2 ug) at lane 5 all for 1 hour at 4 C. After 1 hour of incubation, the digestion reaction was stopped with 0.5 ul of 0.1 M PMSF. Each incubation was examined by running 7.5% SDS-PAGE.

FIG. 4 shows the adipose tissue disruption using ColH (E451D) injection. Fat pad treated are located behind rat hind legs. Left side fat pad was injected with 5 unit E451D diluted in saline, right side with saline only.

FIG. 5 shows the rat fat pad reduction using ColH-FM and hyroxysome topical cream (results from dissection). Fat pad weight is in gram.

FIG. 6 shows the scar reduction using ColH (E451D) and hyroxysome topical cream.

EXPERIMENTS AND EXAMPLES

1. Cloning of ColH (GST-ColH, Using pGEX5T-3 Plasmid)

1) DNA of ColH from Dr. Matsushita of Kagawa Medical School, Japan (2 ug, pCHC11)

2) PCR using primers below to get a 2.95 kb DNA fragment (A87) using ColH DNA as template (from Dr. Matsushita).

```
YO181: AAAGGATCCGTACAAAATGAAAGT
(SEQ ID NO: 4)

YO182: AAACTCGAGTTATCTTCCTACTGAACC
(SEQ ID NO: 5)
```

3) Cut fragment A87 and vector pGEX-5T-3 with restriction enzymes (from New England Biolabs) BamH1 and Xhol. Ligated the cut vector and fragment. Transformed TOP10 cells and plated on Ampicillin (0.1 mg/ml) agarose plate.

4) One colony from the plate had the right sequence of wild type ColH after mini-prep and DNA sequencing.

5) Transformed BL21(E3)/pLysS (from Invitrogen) with pGEX5T-3-ColH (wild type).

2) Introducing E451D mutant.

a) PCR

Fragment 4: PCR Using primers as below, ColH Wild Type cDNA as template:

```
YO181: AAAGGATCCCCGTACAAAATGAAAGT
(SEQ ID NO: 4)
```

-continued

```
YO208: CCTGCAAATAAATCTGCTCCACCTTCTTCATACCAAG
(SEQ ID NO: 6)
```

Fragment 5: PCR Using primers as below, ColH Wild Type cDNA as template:

```
YO209: GTGGAGCAGATTTATTTGCAGGTTCTACTAGAACTTC
(SEQ ID NO: 7)

YO182: AAACTCGAGTTATCTTCCTACTGAACC
(SEQ ID NO: 5)
```

Fragment 6: PCR Using primers as below, Fragment 1 and 2 as template:

```
YO181: AAAGGATCCCCGTACAAAATGAAAGT
(SEQ ID NO: 4)

YO182: AAACTCGAGTTATCTTCCTACTGAACC
(SEQ ID NO: 5)
``` b) Cut Fragment 6 and vector pGEX-5T-3 with restriction enzymes (from New England Biolabs) BamH1 and Xhol. Ligated the cut vector and fragment. Transformed TOP10 cells and plated on Ampicillin (0.1 mg/ml) agarose plate.

c) One colony from the plate had the right sequence of ColH E451D after mini-prep and DNA sequencing.

d) Transformed BL21(E3)/pLysS (from Invitrogen) with pGEX5T-3-ColH (E451D), plated on agarose plate with ampicillin (01 mg/ml) and chroniphenical (0.1 mg/ml).

Conclusion: Both wild type and mutant ColH plasmids were sequenced to verify the sequence authenticity.

3) Introduction of CKGGRAKDC-GG, SEQ ID NO: 8, to the N-terminal of Mutant ColH (E451D) (called ColH-FM)

1) PCR using primers below to get a 2.95 kb DNA fragment (A87) using pGEX5T-3-ColH (E451D) as template (in the above section).

```
LH1:
AAAGGATCCTGTAAGGGAGGAAGAGCTAAGGATTGTGGAGGAGTACAAA

ATGAAAGT
(SEQ ID NO: 9)

LH2:
AAACTCGAGTTATCTTCCTACTGAACC
(SEQ ID NO: 5)
```

2) Cut fragment LH12 and vector pGEX-5T-3 with restriction enzymes (from New England Biolabs) BamH1 and Xhol. Ligated the cut vector and fragment. Transformed DH5α cells and plated on Ampicillin (0.1 mg/ml) agarose plate.

3) Picked colonies and mini-prep to get DNA and then sequence.

4) Transformed BL21(E3)/pLysS (from Invitrogen) with pGEX5T-3-modified ColH (E451 D).

2. Purification

Reagents:

PGEX5T-3-ColH 451 mutant and pGEX5T-3-modified ColH (E451D)

LB broth (autoclaved)

IPTG, (Ampicillin, Chroniphenical, DTT, PMSF.

Glutathione Agarose Beads (50% slurry in ethanol, Pharmacia)

Factor Xa (Amershan Bioscience, 400 unit, diluted to 1 unit/ul in H2O, 4 degree)

Lysis Buffer: PBS+0.1% NP40+5 mM DTT+0.1 mM PMSF
Wash buffer: PBS+5 mM DTT
Cleavage buffer: 50 mM Tris pH 8.0, 100 mM NaCl, 2.5 mM CaCl2+1 mM DTT
Methods:
1) Streak a new LB+Ampicillin (0.1 mg/ml)+Chroniphenical (0.1 mg/ml) agarose plate with glycerol stock of pGEX5T-3-ColH 451. 37 C incubator, overnight.
2) Pick one colony, and start a 5 ml LB+Amp+ Chroniphenical culture, shake at 37 C for 4 hours.
3) Transfer 5 ml culture to 100 ml of LB+Amp+ Chroniphenical culture flask, shake at 37 C overnight.
4) Inoculate 4×1 L of LB+Amp+Chroniphenical culture flask (in 2.8 L large flask) with 4×25 ml overnight culture, shake at 37 C, induce with IPTG (0.2 mM) at O.D. 600=0.6–1.
5) Shake over night around 16 hours at room temperature.
6) Harvest the cells by centrifuge at 500 rpm, 10 minutes.
7) Resuspend in 40 ml Lysis buffer, 4 C.
8) Break the cells by sonication, 4 C.
9) Centrifuge at 17000 rpm, 30 minutes, 4 C. Save the supernatant in 50 ml Falcon tube.
10) Add 4 ml of 50% Glutathione agarose beads in to the supernatant tube. Incubate at 4 C overnight.
11) Pour all of supernatant and beads into a small column. Wash with Wash buffer 10 ml each time 3 times, 4 C.
12) Wash column once with 10 ml cleavage buffer, 4 C.
13) Close the bottom of the column, put 200 ul (Factor Xa, 1 unit/1 ul) in 4 ml cleavage buffer in the column, 4 C. Incubate at 4 C over night. Factor Xa: 1 unit cleaves around 100 ug of GST tagged protein at 4 C in cleavage buffer overnight.
14) Elute the protein by opening up the bottom of the column, save the flow through in a 15 ml falcon tube. Wash the column once more with 2 ml cleavage buffer, save the flow through in the same 15 ml falcon tube.
Conclusion: purity was around 90% after one step affinity purification.

3. Activity Assay on Mutant ColH and Modified Mutant ColH
Reagents
0.05 M TES [tris(hydroxymethyl)-methyl-2-aminoethane sulfonate] buffer with 0.36 mM calcium chloride, pH 7.5
4% Ninhydrin in methyl cellosolve
0.2 M Sodium citrate with 0.71 mM stannous chloride, pH 5.0
Ninhydrin-citric acid mixture: Prepare by mixing 50 ml of the 4% ninhydrin in methyl cellusolve with 50 ml of 0.2 M citrate with 0.71 mM stannous chloride, pH 5.0. Allow mixture to stir for 5 minutes.
50% n-Propanol
Substrate: Worthington bovine achilles tendon collagen (Code: CL) and vitamin free casein
Procedure
1) Weigh 25 mg of Worthington bovine collagen into each of five test tubes. Include at least two tubes to serve as blanks, which will contain no enzyme.
2) Add 5.0 ml of 0.05 M TES buffer to the tubes and incubate at 37° C. for 15 minutes. Start the reaction by adding 0.1 ml of commercial collagnease or mutant ColH enzyme dilution (at different concentrations) to appropriate tubes.
3) After 5 hours, stop the collagenase reaction by transferring 0.2 ml of solution (leaving behind the collagen) to test tubes containing 1.0 ml of ninhydrin-citric acid mixture. Include an enzyme blank (collagen incubated with 0.1 ml TES buffer in place of enzyme).
4) Heat for 20 minutes in a boiling water bath. After cooling, dilute with 5 ml of 50% n-propanol. Let stand for 15 minutes and read absorbance at 600 nm. From an L-leucine standard curve determine micromoles amino acid equivalent to leucine liberated.
Conclusion: E451D was 20% of collagenase activity from Worthington-biochem.

4. Stability Experiments on ColH Variants
Use protease Trypsin to evaluate the stability of ColH.
1) Make 1 ug/ul Trypsin (from Sigma)
2) Put 10 ug of wild type or mutant ColH in an eppendorf tube, dilute to 1 ug/ul with PBS.
3) For each type of protein, in tube 1, add 0.5 ul of 1 ug/ul Trypsin; in tube 2, add 1 ul of 1 ug/ul Trypsin; in tube 3, add 2 ul of 1 ug/ul Trypsin.
4) Incubate on ice for 1 hour.
5) Run 7.5% SDS PAGE.
Conclusion: E451D was twice as stable as wild type ColH.

5. Fat Rat Experiment on Mutant ColH (E451D) in Melting Fat (Injection)
a) Fat Rat Feeding Protocol
Buy S.D. rats at around 50 g. Feed with the following:
Food to feed: every 100 g of basic food, add pork fat 10 g, milk powder 125 g, egg 60 g, fish oil 10 drops. For the first 1-2 week, each rat gets 13 g of food per day. At week 3, each rat gets 15 g each day. At week 4, each rat gets 17 g each day. So on and so forth. After week 8, the rats are around 200-300 g, ready for experiments.
b) Injection Protocol
0.1 ml of the liquid was injected on each fat pad at hind leg.
It was generally observed that a dose of between about 3 to about 50 ABC units of collagenase per fat pad when injected percutaneously effectively melt the injection side of the fat pad in 24 hours, with very little hemorrhage. It was observed that as the dose was increased, the melting fat effect and the amount of interstitial hemorrhage tended to increase. Dosages of over 50 ABC units and higher resulted in considerable local hemorrhage, but at dosages of 5 to 50 ABC units hemorrhage was very minimum to none.
Animal Model
S.D. rat, male and female.
Mutant E451D ColH Material Used
ABC units collagenase per gram: 163,000
Solvent: sterile normal saline
Anesthesia, injection through stomach (I.P.)
Procedure
The rats were anesthetized by intraperitoneal injection. With each male rat, one fat pad behind one leg was injected with saline, one fat pad behind the other leg was injected with mutant collagenase ColH E451D, 5 unit Additional injections with the same activity unit will be undertaken after two days or three days.
20 S.D. fat rats, 10 female, 10 male (after 8 weeks of feeding starting from 50 g), weighted from 200-300 g. They were injected with ColH E451D at 5 u with 5 different protocols. Each protocol covers 4 rats, 2 female and 2 male.
Experiment A
No. of rats: Four S.D. rats, 2 female and 2 male
Rat 1: male, 261 g; rat 2: male, 312 g; rat 3: female, 232 g; rat 4: female, 239 g.
Test solutions: 5 u ColH E451D in 0.1 mL saline
22 gauge, 8" needle used
Injections: Solutions slowly infused into fat pad, moving needle. Day 1
Results: Four rats autopsied on Day 3.
Site 1 (one side behind hind leg): saline: Normal fat pad observed.
Site 2 (the other side behind hind leg): 5 u.

Most of fat melted in the area of injection. Very little bleeding is observed. Muscle membrane is not affected. Considerable amount of oily substance observed in the injected sites, which would reflect a reduction or disruption of fat cells.

Experiment B

No. of rats: Four S.D. rats, 2 female and 2 male

Rat 1: male, 256 g; rat 2: male, 249 g; rat 3: female, 221 g; rat 4: female, 250 g.

Test solutions: 5 u ColH E451D in 0.1 mL saline 22 gauge, 8" needle used

Injections: Solutions slowly infused into fat pad, moving needle. day 1

Results: Four rats autopsied on Day 4.

Site 1 (one side behind hind leg): saline: Normal fat pad observed.

Site 2 (the other side behind hind leg): 5 u.

Fat around injection area is completely melted. Surrounding fat is fragile and detached.

Muscle membrane is not affected. Very little bleeding is observed.

Experiment C

No. of rats: Four S.D. rats, 2 female and 2 male

Rat 1: male, 252 g; rat 2: male, 249 g; rat 3: female, 255 g; rat 4: female, 206 g.

Test solutions: 5 u ColH E451D in 0.1 mL saline 22 gauge, 8" needle used

Injections:

5 u solutions slowly infused into fat pad, moving needle. Day 1

5 u solutions slowly infused into fat pad, moving needle. Day 3

Results: Four rats autopsied on Day 5.

Site 1 (one side behind hind leg): saline: Normal fat pad observed.

Site 2 (the other side behind hind leg): 5 u.

Most of fat melted (more than 50%) in the area of injection. Little bleeding is observed. Considerable amount of oily substance observed in the injected sites. Remaining fat is detached, fragile, and dead.

Experiment D

No. of rats: Four S.D. rats, 2 female and 2 male

Rat 1: male, 240 g; rat 2: male, 253 g; rat 3: female, 244 g; rat 4: female, 266 g.

Test solutions: 5 u ColH E451D in 0.1 mL saline 22 gauge, 8" needle used

Injections:

5 u ColH E451D solutions slowly infused into fat pad, moving needle. Day 1

5 u ColH E451D solutions slowly infused into fat pad, moving needle. Day 4

Results: Four rats autopsied on Day 6.

Site 1 (one side behind hind leg): saline: Normal fat pad observed.

Site 2 (the other side behind hind leg): 5 u.

Fat around injection area was completely melted. Muscle membrane was not affected.

Trace amount of blood was observed.

Rat 1:
weight of fat at saline injection area: 1.46 g;
weight of fat at ColH E451D injection area: 1.09 g.
Rat 2:
weight of fat at saline injection area: 1.28 g;
weight of fat at ColH E451D injection area: 1.17 g.
Rat 3:
weight of fat at saline injection area: 1.43 g;
weight of fat at ColH E451D injection area: 1.16 g.
Rat 4:
weight of fat at saline injection area: 1.47 g;
weight of fat at ColH E451D injection area: 1.23 g.

Experiment E

No. of rats: Four S.D. rats, 2 female and 2 male

Rat 1: male, 240 g; rat 2: male, 266 g; rat 3: female, 216 g; rat 4: female, 238 g.

Test solutions: 5 u ColH E451D in 0.1 mL saline 22 gauge, 8" needle used

Injections:

5 u ColH E451D solutions slowly infused into fat pad, moving needle. Day 1

5 u ColH E451D solutions slowly infused into fat pad, moving needle. Day 3

5 u ColH E451D solutions slowly infused into fat pad, moving needle. Day 5

Results: Four rats autopsied on Day 6.

Site 1 (one side behind hind leg): saline: Normal fat pad observed.

Site 2 (the other side behind hind leg): 5 u.

Fat around injection area is completely melted. Muscle membrane is not affected. Trace amount of blood remains.

Rat 1:
weight of fat at saline injection area: 0.925 g;
weight of fat at ColH E451D injection area: 0.75 g.
Rat 3:
weight of fat at saline injection area: 1.12 g;
weight of fat at ColH E451D injection area: 1.04 g.
Rat 4:
weight of fat at saline injection area: 1.56 g;
weight of fat at ColH E451D injection area: 1.38 g.

6. Fat Rat Experiment on Mutant ColH (E451D) Cream (ColH-FM) Combined with Hydroxysome Transdermal Delivery Method in Melting Fat (Topical)

Research Material 1.1 Experimental Animals:

Male rats, weight 85-95 g, 1 week after stopping breast-feeding.

1.2 Food:

Basic diet is supplied by the animal center. High fat diet composition: 55% basic diet, 12% pork fat, 10% egg, whole fat milk powder 8%, sucrose 5%, peanut 5%, sesame oil 3%, and salt 2%.

1.3 Fat Rat Model Construction:

35 rats were purchased, and fed for a week so that they were familiar with the living environment. These rats later were divided into 2 groups: 1) control rat group (5 rats), fed with basic diet; and 2) fat rat group (30 rats), fed with high fat diet, plus injected under skin 15% MSG saline solution 3 g/kg (once per day), continuously for 5 days. On No. 21 day after the MSG injection, the fat rat group was divided into 6 groups, a) fat rat model group, b) injection high dose group, c) injection median dose group, d) topical high dose group, e) topical median dose group, topical low dose group.

The living environment for these rats were clean, with 12 hours of night time and 12 hours day light each day, with comfortable temperature and good air circulation. Rats could freely eat food and drink water.

1.4 Observation Parameters:

Normal parameters: food intake, urine and faces secretion, and daily activities. Growth parameters: weight, body length, tail length, and Lee's parameters.

1.5 Drug Tested:

1.5.1 HAX solution: freshly prepared at 0.1 g/ml, by dissolving 0.5 g of HAX in 5 ml of experimental distilled water.

1.5.2 Test drug solution: 2.3 ml HAX solution (0.1 g/ml) combined with 2 ml Oulian protein sample (ColH-FM). 5 u Oulian sample (ColH-FM)=18 ul of combined solution.

1.5.3 Control solution: 2.3 ml of HAX (0.1 g/ml) solution combined with 2 ml of PBS or saline solution.

Methods 2.1 Group Division:

30 fat rats were randomly divided into 6 groups, with 5 rats per group. Apply solution drug test solution 1.5.2 and control solution to the fat pad on the reproductive organ.

2.2 Dose and Time Duration:

At each dose for 9 days continuously, the animals were injected with test drug solution or applied topically with test drug solution, once per day. The control groups were only applied with control solution topically each day for 9 days. On the 10$^{th}$ day, rats were killed for evaluation.

2.3 Evaluation:

The efficacy of fat reduction was reviewed by observation with native eye and by measuring the weight of the fat pad at tested region.

Results

The fat reduction dissection figures are shown in FIG. 5.

TABLE 1

Effects of ColH-FM Fat-melting Product on Fat Rat Models (X ± S)

| Group | Rat No. (No.) | Dose Unit/ rat | Rat Start Weight (g) | Rat End Weight (g) | Lee's Parameters | Fat Pad Weight (g) | Fat Removal (%) |
|---|---|---|---|---|---|---|---|
| 1) Control Rat Group | 5 | | 95.5 ± 3.2 | 222.8 ± 16.5 | 291.2 ± 11.6 | 0.99 ± 0.24 | — |
| 2) Fat Rat Control Group | 5 | | 92.3 ± 3.7 | 253.6 ± 28.5 | 315.0 ± 16.3 | 1.24 ± 0.36 | — |
| 3) Injection High-dose Group | 5 | 15 | 96.2 ± 2.9 | 253.1 ± 8.1 | 316.6 ± 14.2 | 0.46 ± 0.11 | 62.9 |
| 4) Injection Median-dose Group | 5 | 10 | 94.5 ± 4.2 | 253.8 ± 21.5 | 315.8 ± 17.5 | 0.65 ± 0.19 | 47.6 |
| 5) Topical High-dose Group | 5 | 15 | 96.5 ± 4.3 | 258.5 ± 25.3 | 316.6 ± 14.2 | 0.63 ± 0.21 | 49.2 |
| 6) Topical Median-dose Group | 5 | 10 | 97.5 ± 3.6 | 256.4 ± 16.9 | 317.6 ± 14.2 | 0.65 ± 0.19 | 47.6 |
| 7) Topical Low-dose Group | 5 | 5 | 94.6 ± 4.1 | 255.2 ± 16.5 | 316.6 ± 14.2 | 0.77 ± 0.29 | 37.9 |

Conclusion:

1) Topical application of ColH-FM (modified mutant collagenase) combined with Hydroxysome transdermal technology is effective in eliminating fat under animal's skin.

2) At median dose (10 unit/rat), the fat-melting efficacy of ColH-FM is similar between injection and topical applications.

7. Human Experiment on Mutant ColH (E451D) Cream Combined with Hydroxysome Transdermal Delivery Method in Melting Fat (Topical)

Human test on ColH-FM cream was conducted in Beijing, China in October 2005. The physician is Dr. Yu, Hai Zhou. 15 obese objects were tested with CoH-FM cream at different activity units for 2 weeks in the fat stomach area, by applying the cream once a day in the night. Using ultrasound to test fat tissue thickness, we obtained the results below.

TABLE 2

Effects of ColH-FM Fat-melting Product on Human Subjects
Summary of Human Test of Mutant Collagenase as Topical Application
China, October 2005

| NAME | COL UNIT | Fat Thickness CHANGE (mm) | BLOOD LIPIDS | FEEDBACK ON SKIN HOT | TIGHTENING | LOOSE | INCREASED APPETITE |
|---|---|---|---|---|---|---|---|
| VAN, Fazhen | 40 | −2 | normal | no | 2-4 d | 5 d-end | 5 d-end |
| YU, Yinchun | 40 | −2 | normal | 1-2 d | 4-5 d | 7 d-end | 6 d |
| CHEN, Shizhen | 40 | −3 | normal | 1-2 d | 4-5 d | 6 d-end | 4 d |

TABLE 2-continued

Effects of ColH-FM Fat-melting Product on Human Subjects
Summary of Human Test of Mutant Collagenase as Topical Application
China, October 2005

| NAME | COL UNIT | Fat Thickness CHANGE (mm) | BLOOD LIPIDS | FEEDBACK ON SKIN | | | INCREASED APPETITE |
|---|---|---|---|---|---|---|---|
| | | | | HOT | TIGHTENING | LOOSE | |
| CHENG, Yaqun | 20 | −4 | normal | 1 d | 4-5 d | 6 d-end | no |
| QIN, Ling | 20 | −5 | normal | 3 d | no | no | no |
| FAN, Huiwen | 20 | −4 | normal | 1 d | no | 5 d-end | 4 d |
| WU, Jianchun | 10 | 0 | normal | 1-2 d | 3-4 d | 5 d-end | 4 d |
| ZHUANG, Ming | 10 | 3 | normal | 1-2 d | no | no | no |
| LIU, Wenhua | 10 | −3 | normal | no | no | 6 d-end | 5 d |
| CHENG, Yi | 5 | 0 | normal | 1 d | no | no | no |
| CHEN, Qiping | 5 | 3 | normal | 1 d | no | 7 d | no |
| XU, Juying | 5 | 5 | high | no | no | no | no |
| WANG, Li | 2.5 | 0 | high | no | no | no | no |
| JI, Rongrong | 2.5 | −3 | normal | no | no | no | no |
| SUN, Dongling | 2.5 | 1 | X | 1-2 d | X | X | X |

Conclusion:

1) Topical application of ColH-FM (modified mutant collagenase) combined with Hydroxysome transdermal technology is effective in eliminating fat under human skin.

2) The topical product is safe, not inducing allergy or raise blood lipids.

8. Human Experiment on Mutant Coil (E451D) Cream Combined with Hydroxysome Transdermal Delivery Method in Scar Reduction (Topical)

Usage:
Apply cream (small amount) twice a day on scar area, once in the morning and once at night.

Results:

1) Scar History
Male, 38 years old. The scar at hand area was caused by sharp knife in 1999. The only treatment for the wound at the time was to stop bleeding, no stitches. The size of the scar later formed: length 5 cm, width: 0.8 cm.

2) Results
Before use of cream, the scar was white and its color was quite different from normal skin. The scar was raised.
After the use of cream for 6 days, the color of the scar was close to normal skin and the size of the scar was decreased 40%.
After 30 days of application, the scar was almost flattened, with clear skin texture. Please see FIG. 6.

3) Results from Two Other Test Subjects
Male, 10 year old raised scar on forehead, caused by car accident and inferior treatment. After 40 days of application, the raised scar was almost flattened.
Male, 2 year old raised scar on elbow. After 20 days of application, the raised scar was flattened a certain degree.

REFERENCES

1. Kolonin, M. et al., Reversal of obesity by targeted ablation of adipose tissue, Nature Medicine 10(6), June 2004, p. 625-632.
2. Methods of delivering material into the skin, and composition used there in, U.S. Pat. No. 6,096,324 (Hydroxysome technology)
3. Methods of delivering material into the skin, and composition used there in, U.S. Pat. No. 6,120,782 (Hydroxysome technology)
4. Seglen, P. O. 1976, Preparation of isolated rat liver cells. Methods Cell Biol. 13: 29-83
5. Yoshihara, K., Matsushita, O., Minami, J., and Okabe, A. Cloning and nucleotide sequence analysis of the colH gene from *Clostridium histolyticum* encoding a collagenase and a gelatinase. J. Bacteriol. 176: 6489-6496
6. Wilson, J. J., Matsushita, O., Okabe, A., and Sakon, J. A bacterial collagen-binding domain with novel calcium-binding motif controls domain orientation, EMBO J. 2003, 22 (8): 1743-1752
7. Bond, M. D., and Van Wart, H. E., 1984, Characterization of individual collagenases from *Clostridium histolyticum*. Biochemistry 23: 3085-3091
8. Peterkofsky, B., 1982. Bacterial collagenase. Methods Enzymol. 82: 453-471
9. Angelton, E. L., and Van Wart, H. E. 1988. Preparation and reconstitution with divalent metal ions of class I and class II *Clostridium histolyticum* appocollagenases. Biochemistry 27: 7406-7412
10. Matsushita, O., Jung, C.-M., Minami, J., Katayama, S., Nishi, N., and Okabe A. 1998. A study of the collagenase-binding domain of a 116-kDa *Clostridium histolyticum* collagenase. J. Biol. Chem. 273: 3643-3648
11. Jung, C.-M. et al. Identification of metal ligands in the *Clostridium histolyticum* ColH collagnease, J. Bacteriology, 1999 May: 2816-2822
12. Matsushita, O., Yoshihara, K., Katayama, S.-I., Minami, J., and Okabe, A. 1994. Purification and characterization of a *Clostridium histolyticum* 120-kilodalton collagenase and nucleotide sequence of the corresponding gene. J. Bacteriol. 176: 149-156

The invention claimed is:

1. A method for reducing the amount of adipose tissue at selected locations in the body comprising:
   administering an effective amount of a modified single mutant collagenase ColH-FM- or a peptide that includes the sequence of ColH-FM to adipose tissue or a subject in need of reducing the amount of adipose tissue,
   wherein the ColH-FM is a *Clostridium histolyticum* collagenase ColH having a single substitution corresponding to Glu451Asp of the wild-type ColH and a peptide motif of CKGGRAKDC-G(x) at the N-terminal of said ColH, wherein x is 2 to 6 (SEQ ID NO: 2).

2. A method for reducing or removing lipomas comprising:
   administering an effective amount of a modified single mutant collagenase ColH-FM- or a peptide that includes the sequence of ColH-FM to a lipoma or a subject in need of reducing or removing lipomas,
   wherein the ColH-FM is a *Clostridium histolyticum* collagenase ColH having a single substitution corresponding to Glu451Asp of the wild-type ColH and a peptide motif of CKGGRAKDC-G(x) at the N-terminal of said ColH, wherein x is 2 to 6 (SEQ ID NO: 2).

3. A method for reducing scars comprising:
   administering an effective amount of a modified single mutant collagenase ColH-FM- or a peptide that includes the sequence of ColH-FM to scar tissue or a subject in need of reducing scars,
   wherein the ColH-FM is a *Clostridium histolyticum* collagenase ColH having a single substitution corresponding to Glu451Asp of the wild-type ColH and a peptide motif of CKGGRAKDC-G(x) at the N-terminal of said ColH, wherein x is 2 to 6 (SEQ ID NO: 2).

4. The method of claim 1, wherein the ColH-FM is injected or topically applied.

5. The method of claim 3, wherein the ColH-FM is injected or topically applied.

6. The method of claim 4, wherein the ColH-FM is topically applied using a transdermal delivery system in a formulation of cream, serum, or liquid form.

7. The method of claim 5, wherein the ColH-FM is topically applied using a transdermal delivery system in a formulation of cream, serum, or liquid form.

8. The method of claim 1, wherein the administration step comprises administrating the collagenase ColH-FM in a form of a pharmaceutical composition comprising a pharmaceutically acceptable carrier and ColH-FM.

9. The method of claim 8, wherein the carrier is at least one selected from the group consisting of a saline solution, an aqueous dextran solution, and an aqueous hetastarch solution.

10. The method of claim 1, wherein the collagenase ColH-FM has the sequence of SEQ ID NO: 1.

11. The method of claim 2, wherein the administration step comprises administrating the collagenase ColH-FM in a form of a pharmaceutical composition comprising a pharmaceutically acceptable carrier and ColH-FM.

12. The method of claim 11, wherein the carrier is at least one selected from the group consisting of a saline solution, an aqueous dextran solution, and an aqueous hetastarch solution.

13. The method of claim 2, wherein the collagenase ColH-FM has the sequence of SEQ ID NO: 1.

14. The method of claim 3, wherein the administration step comprises administrating the collagenase ColH-FM in form of a pharmaceutical composition comprising a pharmaceutically acceptable carrier and ColH-FM.

15. The method of claim 14, wherein the carrier is at least one selected from the group consisting of a saline solution, an aqueous dextran solution, and an aqueous hetastarch solution.

16. The method of claim 3, wherein the collagenase ColH-FM has the sequence of SEQ ID NO: 1.

* * * * *

SEQUENCE LISTING

<160> NUMBER OF SEQ ID NOS: 16

<210> SEQ ID NO 1
<211> LENGTH: 936
<212> TYPE: PRT
<213> ORGANISM: Clostridium histolyticum

<400> SEQUENCE: 1

```
Gly Ser Cys Lys Gly Gly Arg Ala Lys Asp Cys Gly Gly Val Gln Asn
1               5                   10                  15

Glu Ser Lys Arg Tyr Thr Val Ser Tyr Leu Lys Thr Leu Asn Tyr Tyr
            20                  25                  30

Asp Leu Val Asp Leu Leu Val Lys Thr Glu Ile Glu Asn Leu Pro Asp
        35                  40                  45

Leu Phe Gln Tyr Ser Ser Asp Ala Lys Glu Phe Tyr Gly Asn Lys Thr
    50                  55                  60

Arg Met Ser Phe Ile Met Asp Glu Ile Gly Arg Arg Ala Pro Gln Tyr
65                  70                  75                  80

Thr Glu Ile Asp His Lys Gly Ile Pro Thr Leu Val Glu Val Val Arg
                85                  90                  95

Ala Gly Phe Tyr Leu Gly Phe His Asn Lys Glu Leu Asn Glu Ile Asn
            100                 105                 110

Lys Arg Ser Phe Lys Glu Arg Val Ile Pro Ser Ile Leu Ala Ile Gln
        115                 120                 125

Lys Asn Pro Asn Phe Lys Leu Gly Thr Glu Val Gln Asp Lys Ile Val
    130                 135                 140

Ser Ala Thr Gly Leu Leu Ala Gly Asn Glu Thr Ala Pro Pro Glu Val
145                 150                 155                 160

Val Asn Asn Phe Thr Pro Ile Leu Gln Asp Cys Ile Lys Asn Ile Asp
                165                 170                 175

Arg Tyr Ala Leu Asp Asp Leu Lys Ser Lys Ala Leu Phe Asn Val Leu
            180                 185                 190

Ala Ala Pro Thr Tyr Asp Ile Thr Glu Tyr Leu Arg Ala Thr Lys Glu
        195                 200                 205

Lys Pro Glu Asn Thr Pro Trp Tyr Gly Lys Ile Asp Gly Phe Ile Asn
    210                 215                 220

Glu Leu Lys Lys Leu Ala Leu Tyr Gly Lys Ile Asn Asp Asn Asn Ser
225                 230                 235                 240

Trp Ile Ile Asp Asn Gly Ile Tyr His Ile Ala Pro Leu Gly Lys Leu
                245                 250                 255

His Ser Asn Asn Lys Ile Gly Ile Glu Thr Leu Thr Glu Val Met Lys
            260                 265                 270

Val Tyr Pro Tyr Leu Ser Met Gln His Leu Gln Ser Ala Asp Gln Ile
        275                 280                 285

Lys Arg His Tyr Asp Ser Lys Asp Ala Glu Gly Asn Lys Ile Pro Leu
    290                 295                 300

Asp Lys Phe Lys Lys Glu Gly Lys Glu Lys Tyr Cys Pro Lys Thr Tyr
305                 310                 315                 320

Thr Phe Asp Asp Gly Lys Val Ile Ile Lys Ala Gly Ala Arg Val Glu
                325                 330                 335

Glu Glu Lys Val Lys Arg Leu Tyr Trp Ala Ser Lys Glu Val Asn Ser
            340                 345                 350

Gln Phe Phe Arg Val Tyr Gly Ile Asp Lys Pro Leu Glu Glu Gly Asn
        355                 360                 365
```

```
Pro Asp Asp Ile Leu Thr Met Val Ile Tyr Asn Ser Pro Glu Glu Tyr
    370                 375                 380

Lys Leu Asn Ser Val Leu Tyr Gly Tyr Asp Thr Asn Asn Gly Gly Met
385                 390                 395                 400

Tyr Ile Glu Pro Glu Gly Thr Phe Phe Thr Tyr Glu Arg Glu Ala Gln
                405                 410                 415

Glu Ser Thr Tyr Thr Leu Glu Glu Leu Phe Arg His Glu Tyr Thr His
            420                 425                 430

Tyr Leu Gln Gly Arg Tyr Ala Val Pro Gly Gln Trp Gly Arg Thr Lys
        435                 440                 445

Leu Tyr Asp Asn Asp Arg Leu Thr Trp Tyr Glu Glu Gly Gly Ala Asp
    450                 455                 460

Leu Phe Ala Gly Ser Thr Arg Thr Ser Gly Ile Leu Pro Arg Lys Ser
465                 470                 475                 480

Ile Val Ser Asn Ile His Asn Thr Thr Arg Asn Asn Arg Tyr Lys Leu
                485                 490                 495

Ser Asp Thr Val His Ser Lys Tyr Gly Ala Ser Phe Glu Phe Tyr Asn
            500                 505                 510

Tyr Ala Cys Met Phe Met Asp Tyr Met Tyr Asn Lys Asp Met Gly Ile
        515                 520                 525

Leu Asn Lys Leu Asn Asp Leu Ala Lys Asn Asn Asp Val Asp Gly Tyr
    530                 535                 540

Asp Asn Tyr Ile Arg Asp Leu Ser Ser Asn Tyr Ala Leu Asn Asp Lys
545                 550                 555                 560

Tyr Gln Asp His Met Gln Glu Arg Ile Asp Asn Tyr Glu Asn Leu Thr
                565                 570                 575

Val Pro Phe Val Ala Asp Asp Tyr Leu Val Arg His Ala Tyr Lys Asn
            580                 585                 590

Pro Asn Glu Ile Tyr Ser Glu Ile Ser Glu Val Ala Lys Leu Lys Asp
        595                 600                 605

Ala Lys Ser Glu Val Lys Lys Ser Gln Tyr Phe Ser Thr Phe Thr Leu
    610                 615                 620

Arg Gly Ser Tyr Thr Gly Gly Ala Ser Lys Gly Lys Leu Glu Asp Gln
625                 630                 635                 640

Lys Ala Met Asn Lys Phe Ile Asp Asp Ser Leu Lys Lys Leu Asp Thr
                645                 650                 655

Tyr Ser Trp Ser Gly Tyr Lys Thr Leu Thr Ala Tyr Phe Thr Asn Tyr
            660                 665                 670

Lys Val Asp Ser Ser Asn Arg Val Thr Tyr Asp Val Phe His Gly
        675                 680                 685

Tyr Leu Pro Asn Glu Gly Asp Ser Lys Asn Ser Leu Pro Tyr Gly Lys
    690                 695                 700

Ile Asn Gly Thr Tyr Lys Gly Thr Glu Ser Ser Val Ser Thr Thr Thr
705                 710                 715                 720

Ala Glu Ile Lys Asp Leu Ser Glu Asn Lys Leu Pro Val Ile Tyr Met
                725                 730                 735

His Val Pro Lys Ser Gly Ala Leu Asn Gln Lys Val Val Phe Tyr Gly
            740                 745                 750

Lys Gly Thr Tyr Asp Pro Asp Gly Ser Ile Ala Gly Tyr Gln Trp Asp
        755                 760                 765

Phe Gly Asp Gly Ser Asp Phe Ser Ser Glu Gln Asn Pro Ser His Val
    770                 775                 780

Tyr Thr Lys Lys Gly Glu Tyr Thr Val Thr Leu Arg Val Met Asp Ser
```

-continued

```
785                 790                 795                 800

Ser Gly Gln Met Ser Glu Lys Thr Met Lys Ile Lys Ile Thr Asp Pro
                805                 810                 815

Val Tyr Pro Ile Gly Thr Glu Lys Glu Pro Asn Asn Ser Lys Glu Thr
            820                 825                 830

Ala Ser Gly Pro Ile Val Pro Gly Ile Pro Val Ser Gly Thr Ile Glu
        835                 840                 845

Asn Thr Ser Asp Gln Asp Tyr Phe Tyr Phe Asp Val Ile Thr Pro Gly
    850                 855                 860

Glu Val Lys Ile Asp Ile Asn Lys Leu Gly Tyr Gly Gly Ala Thr Trp
865                 870                 875                 880

Val Val Tyr Asp Glu Asn Asn Asn Ala Val Ser Tyr Ala Thr Asp Asp
                885                 890                 895

Gly Gln Asn Leu Ser Gly Lys Phe Lys Ala Asp Lys Pro Gly Arg Tyr
            900                 905                 910

Tyr Ile His Leu Tyr Met Phe Asn Gly Ser Tyr Met Pro Tyr Arg Ile
        915                 920                 925

Asn Ile Glu Gly Ser Val Gly Arg
    930                 935

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (10)..(15)
<223> OTHER INFORMATION: This region may encompass 2-6 Gly residues

<400> SEQUENCE: 2

Cys Lys Gly Gly Arg Ala Lys Asp Cys Gly Gly Gly Gly Gly Gly
1               5                   10                  15

<210> SEQ ID NO 3
<211> LENGTH: 12
<212> TYPE: PRT
<213> ORGANISM: Clostridium histolyticum

<400> SEQUENCE: 3

Asp Arg Leu Thr Trp Tyr Glu Glu Gly Gly Ala Glu
1               5                   10

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aaaggatccc cgtacaaaat gaaagt                                          26

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 5
aaactcgagt tatcttccta ctgaacc                                          27

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cctgcaaata aatctgctcc accttcttca taccaag                               37

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtggagcaga tttatttgca ggttctacta gaacttc                               37

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Lys Gly Gly Arg Ala Lys Asp Cys Gly Gly
1               5                   10

<210> SEQ ID NO 9
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aaaggatcct gtaagggagg aagagctaag gattgtggag gagtacaaaa tgaaagt        57

<210> SEQ ID NO 10
<211> LENGTH: 925
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Ser Val Gln Asn Glu Ser Lys Arg Tyr Thr Val Ser Tyr Leu Lys
1               5                   10                  15

Thr Leu Asn Tyr Tyr Asp Leu Val Asp Leu Leu Val Lys Thr Glu Ile
                20                  25                  30

Glu Asn Leu Pro Asp Leu Phe Gln Tyr Ser Ser Asp Ala Lys Glu Phe
            35                  40                  45

Tyr Gly Asn Lys Thr Arg Met Ser Phe Ile Met Asp Glu Ile Gly Arg
        50                  55                  60
```

```
Arg Ala Pro Gln Tyr Thr Glu Ile Asp His Lys Gly Ile Pro Thr Leu
 65                  70                  75                  80

Val Glu Val Val Arg Ala Gly Phe Tyr Leu Gly Phe His Asn Lys Glu
                 85                  90                  95

Leu Asn Glu Ile Asn Lys Arg Ser Phe Lys Glu Arg Val Ile Pro Ser
             100                 105                 110

Ile Leu Ala Ile Gln Lys Asn Pro Asn Phe Lys Leu Gly Thr Glu Val
         115                 120                 125

Gln Asp Lys Ile Val Ser Ala Thr Gly Leu Leu Ala Gly Asn Glu Thr
130                 135                 140

Ala Pro Pro Glu Val Val Asn Asn Phe Thr Pro Ile Leu Gln Asp Cys
145                 150                 155                 160

Ile Lys Asn Ile Asp Arg Tyr Ala Leu Asp Asp Leu Lys Ser Lys Ala
                165                 170                 175

Leu Phe Asn Val Leu Ala Ala Pro Thr Tyr Asp Ile Thr Glu Tyr Leu
            180                 185                 190

Arg Ala Thr Lys Glu Lys Pro Glu Asn Thr Pro Trp Tyr Gly Lys Ile
        195                 200                 205

Asp Gly Phe Ile Asn Glu Leu Lys Lys Leu Ala Leu Tyr Gly Lys Ile
210                 215                 220

Asn Asp Asn Asn Ser Trp Ile Ile Asp Asn Gly Ile Tyr His Ile Ala
225                 230                 235                 240

Pro Leu Gly Lys Leu His Ser Asn Asn Lys Ile Gly Ile Glu Thr Leu
                245                 250                 255

Thr Glu Val Met Lys Val Tyr Pro Tyr Leu Ser Met Gln His Leu Gln
            260                 265                 270

Ser Ala Asp Gln Ile Lys Arg His Tyr Asp Ser Lys Asp Ala Glu Gly
        275                 280                 285

Asn Lys Ile Pro Leu Asp Lys Phe Lys Glu Gly Lys Glu Lys Tyr
290                 295                 300

Cys Pro Lys Thr Tyr Thr Phe Asp Asp Gly Lys Val Ile Ile Lys Ala
305                 310                 315                 320

Gly Ala Arg Val Glu Glu Lys Val Lys Arg Leu Tyr Trp Ala Ser
                325                 330                 335

Lys Glu Val Asn Ser Gln Phe Phe Arg Val Tyr Gly Ile Asp Lys Pro
            340                 345                 350

Leu Glu Glu Gly Asn Pro Asp Asp Ile Leu Thr Met Val Ile Tyr Asn
        355                 360                 365

Ser Pro Glu Glu Tyr Lys Leu Asn Ser Val Leu Tyr Gly Tyr Asp Thr
370                 375                 380

Asn Asn Gly Gly Met Tyr Ile Glu Pro Glu Gly Thr Phe Phe Thr Tyr
385                 390                 395                 400

Glu Arg Glu Ala Gln Glu Ser Thr Tyr Thr Leu Glu Glu Leu Phe Arg
                405                 410                 415

His Glu Tyr Thr His Tyr Leu Gln Gly Arg Tyr Ala Val Pro Gly Gln
            420                 425                 430

Trp Gly Arg Thr Lys Leu Tyr Asp Asn Asp Arg Leu Thr Trp Tyr Glu
        435                 440                 445

Glu Gly Gly Ala Asp Leu Phe Ala Gly Ser Thr Arg Thr Ser Gly Ile
450                 455                 460

Leu Pro Arg Lys Ser Ile Val Ser Asn Ile His Asn Thr Thr Arg Asn
465                 470                 475                 480

Asn Arg Tyr Lys Leu Ser Asp Thr Val His Ser Lys Tyr Gly Ala Ser
                485                 490                 495
```

```
Phe Glu Phe Tyr Asn Tyr Ala Cys Met Phe Met Asp Tyr Met Tyr Asn
            500                 505                 510
Lys Asp Met Gly Ile Leu Asn Lys Leu Asn Asp Leu Ala Lys Asn Asn
            515                 520                 525
Asp Val Asp Gly Tyr Asp Asn Tyr Ile Arg Asp Leu Ser Ser Asn Tyr
        530                 535                 540
Ala Leu Asn Asp Lys Tyr Gln Asp His Met Gln Glu Arg Ile Asp Asn
545                 550                 555                 560
Tyr Glu Asn Leu Thr Val Pro Phe Val Ala Asp Asp Tyr Leu Val Arg
            565                 570                 575
His Ala Tyr Lys Asn Pro Asn Glu Ile Tyr Ser Glu Ile Ser Glu Val
            580                 585                 590
Ala Lys Leu Lys Asp Ala Lys Ser Glu Val Lys Ser Gln Tyr Phe
            595                 600                 605
Ser Thr Phe Thr Leu Arg Gly Ser Tyr Thr Gly Gly Ala Ser Lys Gly
        610                 615                 620
Lys Leu Glu Asp Gln Lys Ala Met Asn Lys Phe Ile Asp Asp Ser Leu
625                 630                 635                 640
Lys Lys Leu Asp Thr Tyr Ser Trp Ser Gly Tyr Lys Thr Leu Thr Ala
            645                 650                 655
Tyr Phe Thr Asn Tyr Lys Val Asp Ser Ser Asn Arg Val Thr Tyr Asp
            660                 665                 670
Val Val Phe His Gly Tyr Leu Pro Asn Glu Gly Asp Ser Lys Asn Ser
        675                 680                 685
Leu Pro Tyr Gly Lys Ile Asn Gly Thr Tyr Lys Gly Thr Glu Ser Ser
        690                 695                 700
Val Ser Thr Thr Thr Ala Glu Ile Lys Asp Leu Ser Glu Asn Lys Leu
705                 710                 715                 720
Pro Val Ile Tyr Met His Val Pro Lys Ser Gly Ala Leu Asn Gln Lys
            725                 730                 735
Val Val Phe Tyr Gly Lys Gly Thr Tyr Asp Pro Asp Gly Ser Ile Ala
            740                 745                 750
Gly Tyr Gln Trp Asp Phe Gly Asp Gly Ser Asp Phe Ser Ser Glu Gln
            755                 760                 765
Asn Pro Ser His Val Tyr Thr Lys Lys Gly Glu Tyr Thr Val Thr Leu
        770                 775                 780
Arg Val Met Asp Ser Ser Gly Gln Met Ser Glu Lys Thr Met Lys Ile
785                 790                 795                 800
Lys Ile Thr Asp Pro Val Tyr Pro Ile Gly Thr Glu Lys Glu Pro Asn
            805                 810                 815
Asn Ser Lys Glu Thr Ala Ser Gly Pro Ile Val Pro Gly Ile Pro Val
            820                 825                 830
Ser Gly Thr Ile Glu Asn Thr Ser Asp Gln Asp Tyr Phe Tyr Phe Asp
        835                 840                 845
Val Ile Thr Pro Gly Glu Val Lys Ile Asp Ile Asn Lys Leu Gly Tyr
        850                 855                 860
Gly Gly Ala Thr Trp Val Val Tyr Asp Glu Asn Asn Asn Ala Val Ser
865                 870                 875                 880
Tyr Ala Thr Asp Asp Gly Gln Asn Leu Ser Gly Lys Phe Lys Ala Asp
            885                 890                 895
Lys Pro Gly Arg Tyr Tyr Ile His Leu Tyr Met Phe Asn Gly Ser Tyr
            900                 905                 910
Met Pro Tyr Arg Ile Asn Ile Glu Gly Ser Val Gly Arg
```

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Cys Lys Gly Gly Arg Ala Lys Asp Cys
1               5

<210> SEQ ID NO 12
<211> LENGTH: 2946
<212> TYPE: DNA
<213> ORGANISM: Clostridium histolyticum

<400> SEQUENCE: 12

```
gtacaaaatg aaagtaagag gtatacagta tcatatttaa agactttaaa ttattatgac      60
ttagtagatt tgcttgttaa gactgaaatt gagaatttac cagacctttt tcagtatagt     120
tcagatgcaa aagagttcta tggaaataaa actcgtatga gctttatcat ggatgaaatt     180
ggtagaaggg cacctcagta tacagagata gatcataaag gtattcctac tttagtagaa     240
gttgtaagag ctggatttta cttaggattc cataacaagg aattgaatga aataaacaag     300
aggtctttta aagaaagggt aatacttct atattagcaa ttcaaaaaaa tcctaatttt     360
aaactaggta ctgaagttca agataaaata gtatctgcaa caggactttt agctggtaat     420
gaaacagcgc ctccagaagt tgtaaataat tttacaccaa tacttcaaga ctgtataaag     480
aatatagaca gatacgctct tgatgattta aagtcaaaag cattatttaa tgttttagct     540
gcacctacct atgatataac tgagtattta gagctacta aagaaaaacc agaaaacact     600
ccttggtatg gtaaaataga tgggtttata aatgaactta aaaagttagc tctttatgga     660
aaaataaatg ataataactc ttggataata gataacggta tatatcatat agcacctta     720
gggaagttac atagcaataa taaaatagga atagaaactt taacagaggt tatgaaagtt     780
tatcccttatt taagtatgca acatttacaa tcagcagatc aaattaagcg tcattatgat     840
tcaaaagatg ctgaaggaaa caaaatacct ttagataagt ttaaaaagga aggaaaagaa     900
aaatactgtc caaaaactta tacatttgat gatggaaaag taataataaa agctggtgct     960
agagtagaag aagaaaaagt taaaagacta tactgggcat caaaggaagt taactctcaa    1020
ttctttagag tatacggaat agacaaacca ttagaagaag gtaatccaga tgatatatta    1080
acaatggtta tctacaacag tcccgaagaa tataaactca atagtgttct atacggatat    1140
gatactaata atggtggtat gtatatagag ccagaaggaa ctttcttcac ctatgaaaga    1200
gaagctcaag aaagcacata cattgaaga gaattattta gacatgaata tacacattat    1260
ttgcaaggaa gatatgcagt tccaggacaa tggggaagaa caaaacttta tgacaatgat    1320
agattaactt ggtatgaaga aggtggagca gatttatttg caggttctac tagaacttct    1380
ggaatattac caagaaagag tatagtatca aatattcata atacaacaag aaataataga    1440
tataagcttt cagacactgt acattctaaa atggtgcta gtttttgaatt ctataattat    1500
gcatgtatgt ttatggatta tgtataat aaagatatgg gtatattaaa taaactaaat    1560
gatcttgcaa aaaataatga tgttgatgga tatgataatt atattagaga tttaagttct    1620
aattatgctt taaatgataa atatcaagat catatgcagg agcgcataga taattatgaa    1680
```

-continued

```
aatttaacag tgccttttgt agctgatgat tatttagtaa ggcatgctta taagaaccct      1740
aatgaaattt attctgaaat atctgaagta gcaaaattaa aggatgctaa gagtgaagtt      1800
aagaaatcac aatattttag taccttact ttgagaggta gttacacagg tggagcatct       1860
aaggggaaat tagaagatca aaaagcaatg aataagttta tagtgattc acttaagaaa       1920 ttagatacgt attcttggag tgggtataaa actttaactg cttatttcac taattataaa     1980
gttgactctt caaatagagt tactatgat gtagtattcc acggatattt accaaacgaa      2040
ggtgattcca aaaattcatt accttatggc aagatcaatg gaacttacaa gggaacagag     2100
aaagaaaaaa tcaaattctc tagtgaaggc tctttcgatc cagatggtaa aatagtttct     2160
tatgaatggg atttcggaga tggtaataag agtaatgagg aaaatccaga gcattcatat     2220
gacaaggtag gaacttatac agtgaaatta aagttactg atgacaaggg agaatcttca      2280
gtatctacta ctactgcaga aataaaggat ctttcagaaa ataaacttcc agttatatat     2340
atgcatgtac ctaaatccgg agccttaaat caaaagttg ttttctatgg aaaaggaaca      2400
tatgacccag atggatctat cgcaggatat caatgggact ttggtgatgg aagtgatttt     2460
agcagtgaac aaaacccaag ccatgtatat actaaaaaag gtaatatac tgtaacatta      2520 agagtaatgg atagtagtgg acaaatgagt gaaaaaacta tgaagattaa gattacagat    2580
ccggtatatc caataggcac tgaaaaagaa ccaataacaa gtaaagaaac tgcaagtggt     2640
ccaatagtac caggtatacc tgttagtgga accatagaaa atacaagtga tcaagattat     2700
ttctattttg atgttataac accaggagaa gtaaaaatag atataaataa attagggtac     2760
ggaggagcta cttgggtagt atatgatgaa aataataatg cagtatctta tgccactgat     2820
gatgggcaaa atttaagtgg aaagtttaag gcagataaac caggtagata ttacatccat     2880
ctttacatgt ttaatggtag ttatatgcca tatagaatta atatagaagg ttcagtagga     2940
agataa                                                                2946
```

<210> SEQ ID NO 13
<211> LENGTH: 2979
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

```
tgtaagggag gaagagctaa ggattgtgga ggagtacaaa atgaaagtaa gaggtataca       60
gtatcatatt taaagacttt aaattattat gacttagtag atttgcttgt taagactgaa     120
attgagaatt taccagacct ttttcagtat agttcagatg caaaagagtt ctatggaaat     180
aaaactcgta tgagctttat catggatgaa attggtagaa gggcacctca gtatacagag     240
atagatcata aaggtattcc tactttagta gaagttgtaa gagctggatt ttacttagga     300
ttccataaca aggaattgaa tgaaataaac aagaggtctt taaagaaag ggtaataccct      360 tctatattag caattcaaaa aaatcctaat tttaaactag gtactgaagt tcaagataaa     420
atagtatctg caacaggact tttagctggt aatgaaacag cgcctccaga agttgtaaat     480
aattttacac caatacttca agactgtata aagaatatag acagatacgc tcttgatgat     540
ttaaagtcaa aagcattatt taatgtttta gctgcaccta cctatgatat aactgagtat     600
ttaagagcta ctaaagaaaa accagaaaac actccttggt atggtaaaat agatgggttt      660
ataaatgaac ttaaaagtt agctctttat ggaaaaataa atgataataa ctcttggata       720
atagataacg gtatatatca tatagcacct ttagggaagt tacatagcaa taataaata      780
```

```
ggaatagaaa ctttaacaga ggttatgaaa gtttatcctt atttaagtat gcaacattta      840
caatcagcag atcaaattaa gcgtcattat gattcaaaag atgctgaagg aaacaaaata      900
cctttagata agtttaaaaa ggaaggaaaa gaaaaatact gtccaaaaac ttatacattt      960
gatgatggaa aagtaataat aaaagctggt gctagagtag aagaagaaaa agttaaaaga     1020
ctatactggg catcaaagga agttaactct caattcttta gagtatacgg aatagacaaa     1080
ccattagaag aaggtaatcc agatgatata ttaacaatgg ttatctacaa cagtcccgaa     1140
gaatataaac tcaatagtgt tctatacgga tatgatacta ataatggtgg tatgtatata     1200
gagccagaag gaactttctt cacctatgaa agagaagctc aagaaagcac atacacatta     1260
gaagaattat ttagacatga atatacacat tatttgcaag gaagatatgc agttccagga     1320 caatgggaa gaacaaaact ttatgacaat gatagattaa cttggtatga agaaggtgga     1380
gcagatttat ttgcaggttc tactagaact tctggaatat taccaagaaa gagtatagta     1440
tcaaatattc ataatacaac aagaaataat agatataagc tttcagacac tgtacattct     1500
aaatatggtg ctagttttga attctataat tatgcatgta tgtttatgga ttatatgtat     1560
aataaagata tgggtatatt aaataaacta atgatcttg caaaaaataa tgatgttgat     1620
ggatatgata attatattag agatttaagt tctaattatg ctttaaatga taaatatcaa     1680
gatcatatgc aggagcgcat agataattat gaaaatttaa cagtgccttt tgtagctgat     1740
gattatttag taaggcatgc ttataagaac cctaatgaaa tttattctga aatatctgaa     1800
gtagcaaaat taaggatgc taagagtgaa gttaagaaat cacaatattt tagtaccttt     1860
actttgagag gtagttacac aggtggagca tctaagggga aattagaaga tcaaaaagca     1920
atgaataagt ttatagatga ttcacttaag aaattagata cgtattcttg gagtgggtat     1980
aaaactttaa ctgcttattt cactaattat aaagttgact cttcaaatag agttacttat     2040
gatgtagtat tccacggata tttaccaaac gaaggtgatt ccaaaaattc attaccttat     2100
ggcaagatca atggaactta caagggaaca gagaaagaaa aaatcaaatt ctctagtgaa     2160
ggctctttcg atccagatgg taaaatagtt tcttatgaat gggatttcgg agatggtaat     2220
aagagtaatg aggaaaatcc agagcattca tatgacaagg taggaactta tacagtgaaa     2280
ttaaaagtta ctgatgacaa gggagaatct tcagtatcta ctactactgc agaaataaag     2340
gatctttcag aaaataaact tccagttata tatatgcatg tacctaaatc cggagcctta     2400
aatcaaaaag ttgttttcta tggaaaagga acatatgacc cagatggatc tatcgcagga     2460
tatcaatggg actttggtga tggaagtgat tttagcagtg aacaaaaccc aagccatgta     2520
tatactaaaa aaggtgaata tactgtaaca ttaagagtaa tggatagtag tggacaaatg     2580
agtgaaaaaa ctatgaagat taagattaca gatccggtat atccaatagg cactgaaaaa     2640
gaaccaaata acagtaaaga aactgcaagt ggtccaatag taccaggtat acctgttagt     2700
ggaaccatag aaaatacaag tgatcaagat tatttctatt ttgatgttat aacaccagga     2760
gaagtaaaaa tagatataaa taaattaggg tacggaggag ctacttgggt agtatatgat     2820
gaaaataata atgcagtatc ttatgccact gatgatgggc aaaatttaag tggaaagttt     2880
aaggcagata aaccaggtag atattacatc catctttaca tgtttaatgg tagttatatg     2940
ccatatagaa ttaatataga aggttcagta ggaagataa                            2979
```

<210> SEQ ID NO 14
<211> LENGTH: 5
<212> TYPE: PRT
<213> ORGANISM: Clostridium histolyticum

```
<220> FEATURE:
<221> NAME/KEY: Misc_feature
<222> LOCATION: (3..4)
<223> OTHER INFORMATION: "Xaa" can be Ala, Cys, Asp, Glu, Phe, Gly,
      His, Ile, Lys, Leu, Met, Asn, Pro, Gln,
      Arg, Ser, Thr, Val, Trp or Tyr

<400> SEQUENCE: 14

His Glu Xaa Xaa His
1               5

<210> SEQ ID NO 15
<211> LENGTH: 6
<212> TYPE: PRT
<213> ORGANISM: Clostridium histolyticum
<220> FEATURE:
<221> NAME/KEY: Misc_feature
<222> LOCATION: (3..5)
<223> OTHER INFORMATION: "Xaa" can be Ala, Cys, Asp, Glu, Phe, Gly,
      His, Ile, Lys, Leu, Met, Asn, Pro, Gln,
      Arg, Ser, Thr, Val, Trp or Tyr

<400> SEQUENCE: 15

His Glu Xaa Xaa Xaa His
1               5

<210> SEQ ID NO 16
<211> LENGTH: 6
<212> TYPE: PRT
<213> ORGANISM: Clostridium histolyticum
<220> FEATURE:
<221> NAME/KEY: Misc_feature
<222> LOCATION: (3..5)
<223> OTHER INFORMATION: "Xaa" can be Ala, Cys, Asp, Glu, Phe, Gly,
      His, Ile, Lys, Leu, Met, Asn, Pro, Gln,
      Arg, Ser, Thr, Val, Trp or Tyr

<400> SEQUENCE: 16

Glu Glu Xaa Xaa Xaa Glu
1               5
```